(12) United States Patent
Shubin, Sr.

(10) Patent No.: US 9,949,866 B2
(45) Date of Patent: Apr. 24, 2018

(54) BIOLOGICAL FLUID COLLECTION SYSTEM

(71) Applicant: Steven A. Shubin, Sr., Dripping Springs, TX (US)

(72) Inventor: Steven A. Shubin, Sr., Dripping Springs, TX (US)

(*) Notice: Subject to any disclaimer, the term of this patent is extended or adjusted under 35 U.S.C. 154(b) by 1129 days.

(21) Appl. No.: 13/836,498

(22) Filed: Mar. 15, 2013

(65) Prior Publication Data

US 2013/0253457 A1   Sep. 26, 2013

Related U.S. Application Data

(60) Provisional application No. 61/612,347, filed on Mar. 18, 2012.

(51) Int. Cl.
*A61F 5/453* (2006.01)
*A61B 10/00* (2006.01)
*A61D 19/02* (2006.01)

(52) U.S. Cl.
CPC .......... *A61F 5/453* (2013.01); *A61B 10/0058* (2013.01); *A61D 19/021* (2013.01)

(58) Field of Classification Search
USPC .......................................................... 604/349
See application file for complete search history.

(56) References Cited

U.S. PATENT DOCUMENTS

| | | |
|---|---|---|
| 4,744,352 A | 5/1988 | Emery |
| 5,437,652 A | 8/1995 | Anatolievich |
| 5,466,235 A | 11/1995 | Shubin, Sr. |
| 5,496,301 A | 3/1996 | Hlavinka et al. |
| 5,782,818 A | 7/1998 | Shubin |
| 5,806,523 A | 9/1998 | Shubin, Sr. |
| 5,807,360 A | 9/1998 | Shubin |

(Continued)

FOREIGN PATENT DOCUMENTS

| | | |
|---|---|---|
| CN | 101193597 | 6/2008 |
| EP | 1897519 | 3/2008 |

(Continued)

OTHER PUBLICATIONS

European Search Report and Communication 1376443.5, dated Nov. 10, 2015 (including patent No. SU 342 388 A1 issued to KH Zooveterinaryj Inst for which there is no available English-language Abstract).

(Continued)

*Primary Examiner* — Todd J Scherbel
*Assistant Examiner* — Guy K Townsend
(74) *Attorney, Agent, or Firm* — Conley Rose PC

(57) ABSTRACT

Biological fluid collection. At least some of the illustrative embodiments are systems including a sleeve of elastomeric material and a receptacle coupled to the sleeve. The sleeve may include: first and second ends, each end comprising respectively a first and a second orifice; and a passage extending between the first and second orifices. The receptacle may include: a side wall and a bottom that define an interior volume and a height; and an entrance portion that defines an internal diameter, wherein the height of receptacle is at least half the internal diameter. The receptacle may mechanically couple to the sleeve such that the interior volume is fluidly coupled to the passage of the sleeve.

5 Claims, 8 Drawing Sheets

(56) References Cited

U.S. PATENT DOCUMENTS

| | | | |
|---|---|---|---|
| 6,149,580 A * | 11/2000 | Dabney | A61H 19/00 600/38 |
| 7,041,064 B2 | 5/2006 | Vayer | |
| 7,186,212 B1 * | 3/2007 | McMullen | A63H 3/003 600/38 |
| 7,435,153 B1 * | 10/2008 | Sodec, Jr. | A47F 8/00 446/295 |
| 7,544,062 B1 * | 6/2009 | Hauschild | G09B 23/285 434/267 |
| 7,753,895 B2 | 7/2010 | Matsuura | |
| 7,947,026 B2 | 5/2011 | Herr et al. | |
| 8,663,087 B2 * | 3/2014 | Kolar | A61H 9/0021 600/38 |
| 2004/0039248 A1 | 2/2004 | Vayer | |
| 2007/0031859 A1 | 2/2007 | Yan et al. | |
| 2010/0041944 A1 * | 2/2010 | Levy | 600/38 |
| 2010/0069706 A1 | 3/2010 | Rousere | |
| 2013/0253457 A1 * | 9/2013 | Shubin, Sr. | A61F 5/453 604/349 |

FOREIGN PATENT DOCUMENTS

| | | |
|---|---|---|
| GB | 767389 | 1/1957 |
| SU | 342 388 | 6/1978 |

OTHER PUBLICATIONS

International Search Report and Written Opinion dated Jul. 18, 2013 in International Patent Application No. PCT/US2013/032758, filed Mar. 18, 2013.

Third Office Action for Chinese Patent Application No. 201380014692.9, dated Feb. 6, 2017.

* cited by examiner

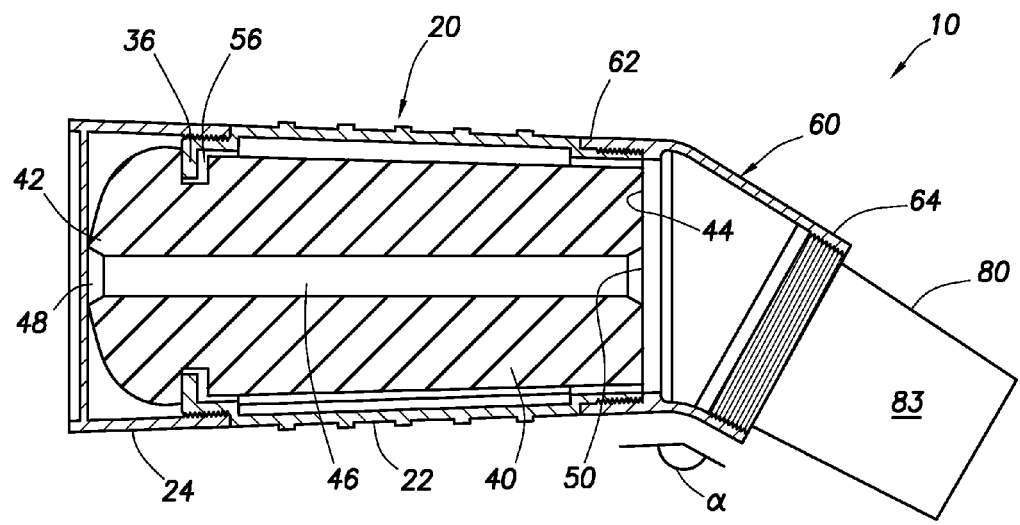
FIG.3
FIG.4
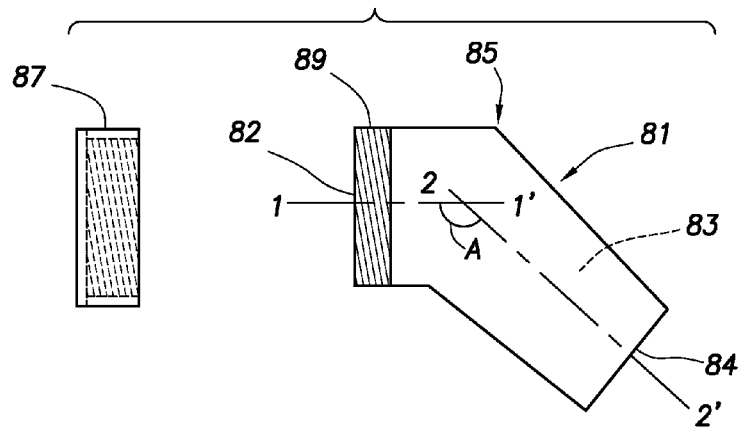

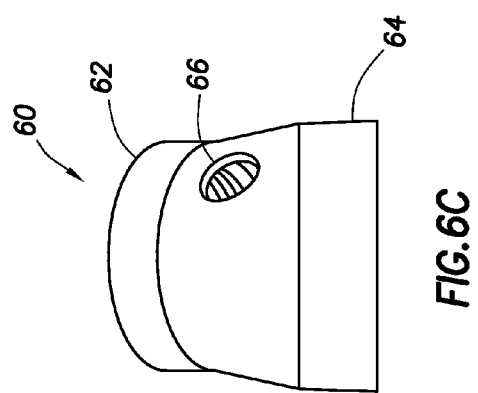
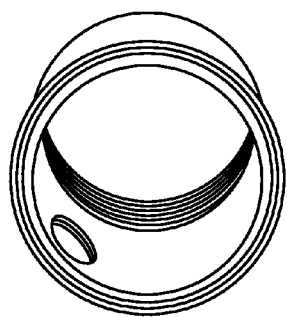
FIG.6D
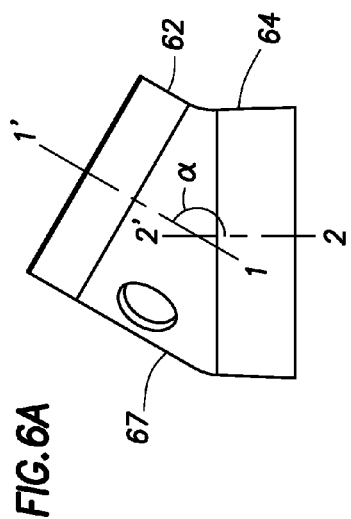
FIG.6A
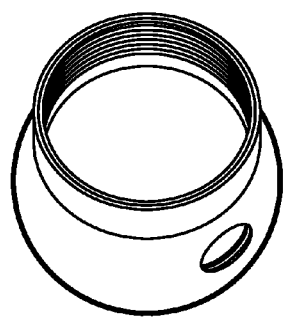
FIG.6E
FIG.6C
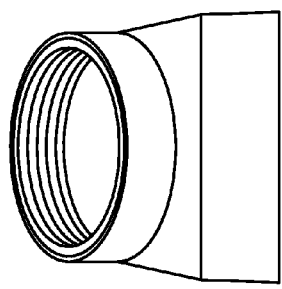
FIG.6B

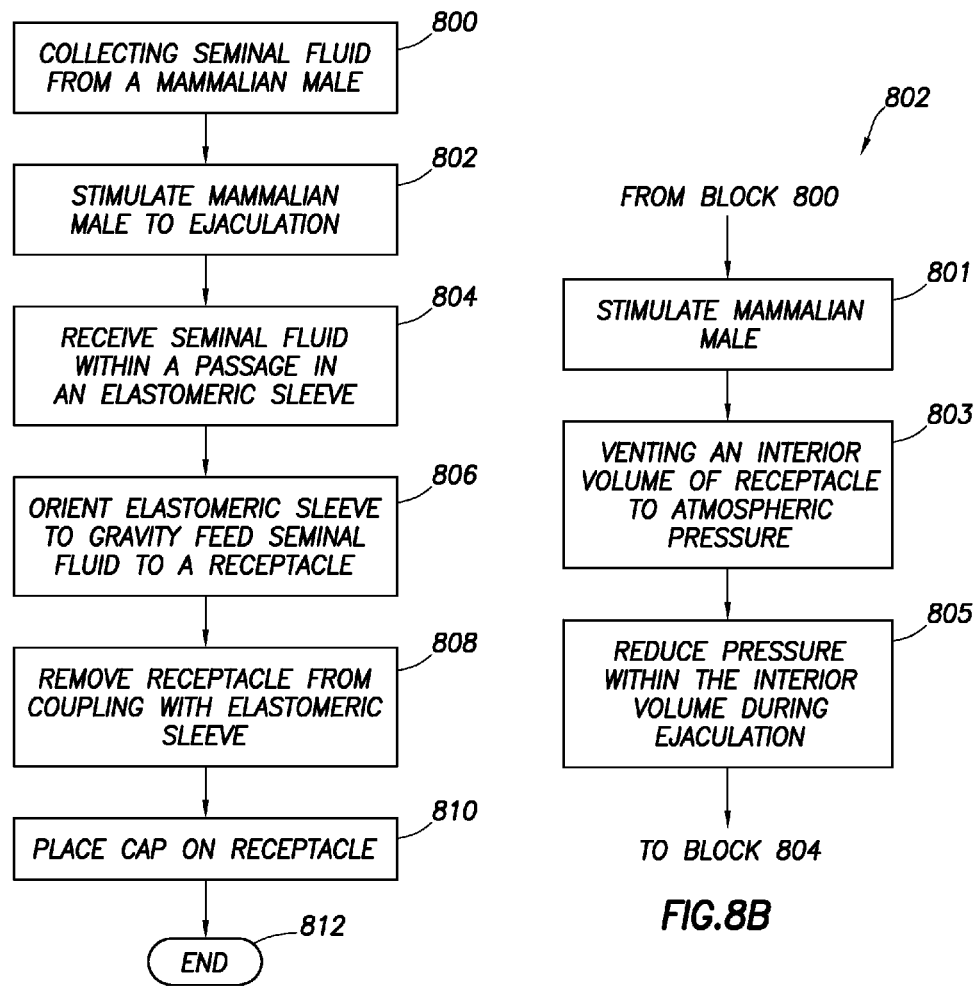

BIOLOGICAL FLUID COLLECTION SYSTEM

CROSS-REFERENCE TO RELATED APPLICATIONS

The present application claims the benefit of U.S. Provisional Patent Application No. 61/612,347 filed Mar. 18, 2012 by Steven A. Shubin Sr., titled "Biological Fluid Collection System," which is incorporated herein by reference as if reproduced in its entirety.

BACKGROUND

A variety of biological fluid collection devices and systems have been developed to assist with or otherwise aid in the production and collection of biological fluids. Included are systems and devices that aid in the stimulation and therefore production of seminal fluid such as masturbation sleeves and other such systems. Examples of such devices are disclosed in: U.S. Pat. No. 5,782,818, issued Jul. 21, 1998, titled "Device for Discreet Sperm Collection"; U.S. Pat. No. 5,806,523, issued Sep. 15, 1998, titled "Prophylactic and Prosthetic Device"; U.S. Pat. No. 5,807,360, issued Sep. 15, 1998, titled "Device for Discreet Sperm Collection"; and U.S. Pat. No. 5,466,235, issued Nov. 14, 1995, titled "Female Functional Mannequin"; all to Steven A. Shubin, Sr. and all of which are incorporated herein by reference in their entirety.

The collection of seminal fluid, whether in humans or animals, can be problematic and difficult. Whether, as is the case with human males collection can be an embarrassing and awkward experience, or as can be the case with male animals, collection can be problematic when attempting to obtain the sample. Further, and in the cases of large animals such as horses and the like, the collection can be dangerous due to the size, unpredictability, and un-cooperation of the animal.

With respect to humans, the procedure is still quite archaic and comprises the individual masturbating into a specimen receptacle, which can lead to discomfort. That is, the erect male penis is generally upwardly oriented, while the collection device must be held or situated lower or downwardly thereto. As such, the donor must force the erect penis downwardly in order for the ejaculate to be received in the specimen container. Forcing the erect penis downwardly not only can be difficult and uncomfortable, but in some cases can also be painful. Further, conflict between the position of the specimen container with respect to the erect penis can then lead to loss of ejaculate and/or inadvertent loss of more sperm rich ejaculate due to improper timing of the onset and/or ejaculation of the male. Whether due to discomfort that may occur during use or the difficulty in the simultaneous angulation and alignment of the specimen container and the penis, improvements are desired.

Yet further, the specimen containers that are used in today's facilities are designed for utilitarian purposes rather than comfort. For example, the specimen container itself functions strictly as a receptacle and offers nothing in the way of comfort, ease of use, or other assistance to and/or for the donor. Still further, the size, shape, rough edges and screw threads of today's specimen containers can actually cause the donor discomfort and even pain if contact with the genitalia is made.

Yet further, the collection of seminal fluid in animals is also problematic and difficult. For these specimens, collection can pose physical dangers to personnel engaged in the collection. As such, devices, systems, and methods that reduce the unpredictability and increase the cooperation of the animal are desired. Further, as the acquired semen specimens are not only used in the diagnoses and treatment of the animal, but may also be sold to breeders and the like, such specimens can be profitable and thus, the owners of these animals seek to have the specimen fully captured with the least amount of waste.

Moreover, doctors say prostate health may benefit from the stimulation of the production of seminal fluid and thus systems that facilitate the process while mitigating the disadvantages previously described are desired. Recent studies have found that prostate health in human males may be related to frequency of ejaculation. In particular, infrequent ejaculation can lead to swelling of the prostate, known as congestive prostatitis, and may also increase the cancer risk in human males. Some medical sources suggest an ejaculation frequency of three to four times per week to ensure good prostate health. One study found a 14% lower lifetime prostate cancer rate for men who ejaculate between 13 and 20 times per month, and a upwards of 33% lower lifetime prostate cancer risk for men who ejaculate 21 times or more each month. Devices for stimulation and collection of seminal fluids may aid achieving higher ejaculations rates among men, particularly the unmarried and long-married.

Beyond assisting with respect to prostate health effects of ejaculation, devices for stimulation and collection of seminal fluids through ejaculation may also assist in reversing desensitization issues. That is, repeated masturbatory stimulation of the penis using the hand or rough cloth can lead to desensitization of the penis, particularly in the absence of lubrication in some form. Desensitization can then result in erectile dysfunction during copulation. Use of properly lubricated devices designed specifically for the stimulation and collection of seminal fluid may help reverse the desensitization issues, and thus reduce the occurrence of erective dysfunction related to the desensitization issue.

BRIEF DESCRIPTION OF THE DRAWINGS

For a detailed description of exemplary embodiments, reference will now be made to the accompanying drawings in which:

FIG. 3 is a side sectional view of an assembled embodiment of the system of FIG. 1;

FIG. 4 is a side view of an angled receptacle according to one embodiment of the disclosure;

FIG. 6A illustrates a perspective view of an adapter according to one embodiment of the disclosure;

FIG. 6B illustrates a perspective view of an adapter according to one embodiment of the disclosure;

FIG. 6C illustrates a perspective view of an adapter according to one embodiment of the disclosure;

FIG. 6D illustrates a perspective view of an adapter according to one embodiment of the disclosure;

FIG. 6E illustrates a perspective view of an adapter according to one embodiment of the disclosure;

FIGS. 8A and 8B illustrate a flowchart of a method in accordance with an embodiment of the disclosure.

NOTATION AND NOMENCLATURE

Figure 1:
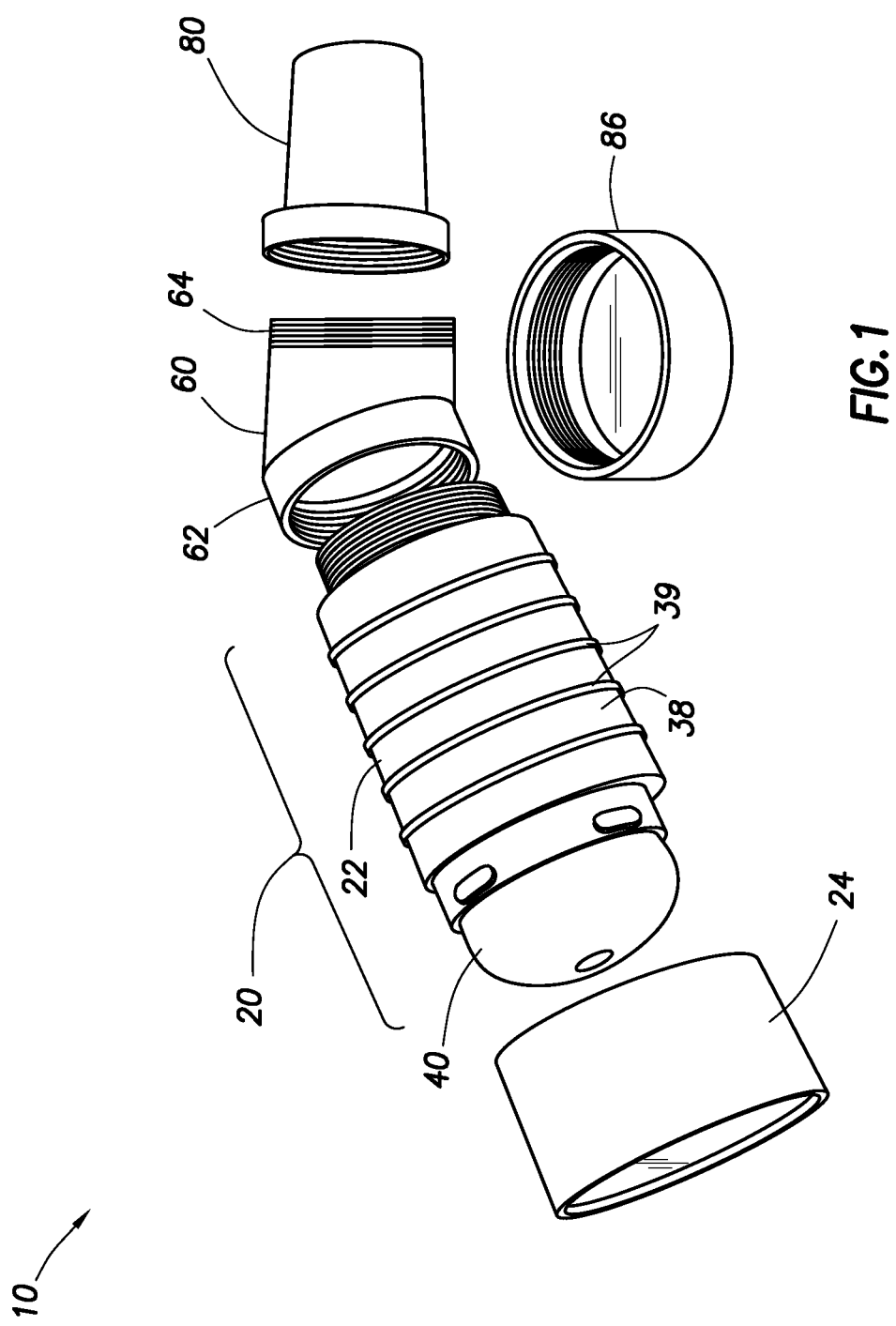
FIG. 1 is a disassembled exploded perspective view of an embodiment of the system of the disclosure.

Certain terms are used throughout the following description and claims to refer to particular system components. As one skilled in the art will appreciate, different companies may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections. Further such connection may be a communicative connection, including but not limited to fluid or other mechanical communication, signal communication or the like, and may, but need not mean physically attached so as to form a single unit when so coupled.

Where specific dimensional and material specifications have been included or omitted from the specification or the claims, or both, it is to be understood that the same are not to be incorporated into the claims, unless so claimed.

For purposes of description herein, the terms "upper", "lower", "above", "below", "right", "left", "rear", "front", "vertical", "horizontal", and derivatives thereof, shall relate to the orientation of the device as shown in FIG. 3.

The same reference numerals may be used throughout the drawings to refer to the same or like parts. Further like features between the various embodiments may utilize similar numerical designations. Where appropriate, the corresponding alphabetic designator has been changed. Further, the dimensions illustrated in the drawings (if provided) are included for purposes of example only and are not intended to limit the scope of the present invention.

"Fluid" is used and defined in a broad, general, and ordinary sense, and the terminology is meant to apply to, inter alia, urine, seminal, and other biological fluids.

Further, the purpose of the Abstract is to enable the United States Patent and Trademark Office, the public, and especially the scientists, engineers, and practitioners in the art who are not familiar with the patent or legal terms of phraseology, to learn quickly, from a cursory inspection, the nature of the technical disclosure of the application. Accordingly, the Abstract is intended to define neither the invention nor the application, which is only measured by the claims, nor is it intended to be limiting as to the scope of the claims in any manner.

DETAILED DESCRIPTION

The following discussion is directed to various embodiments. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The various example embodiments discussed below were developed in the context of collection of human sperm and seminal fluids, and thus the discussion that follows is based on the developmental context; however, the embodiments disclosed herein are not meant to be limited to just collection of human sperm and seminal fluids (unless claimed as such), and the systems, devices, and methods disclosed herein may be utilized with any biological fluid (e.g., urine), as well as the collection of such fluids in non-human animals (e.g., horses).

The collection of biological fluid from male animals can be problematic. In the case with human males, collection can be embarrassing and awkward. In the cases of large animals such as horses, the collection of specimens can pose physical dangers, and thus devices, systems, and methods that reduce the unpredictability and increase the cooperation of the animal are also desired.

The disadvantages and drawbacks of the related-art are addressed, at least in part, through the example system 10 disclosed and described herein. Referring now to FIG. 1, there is shown a fluid collection system 10 which comprises a device 20 including a shell 22 and a sleeve 40, an adapter 60 (which may be equivalently referred to as a connector or elbow), and a receptacle 80 (which may be equivalently referred to as a reservoir or vessel), along with caps 24 and 86 (which may be equivalently referred to as lids or covers).

Figure 2:
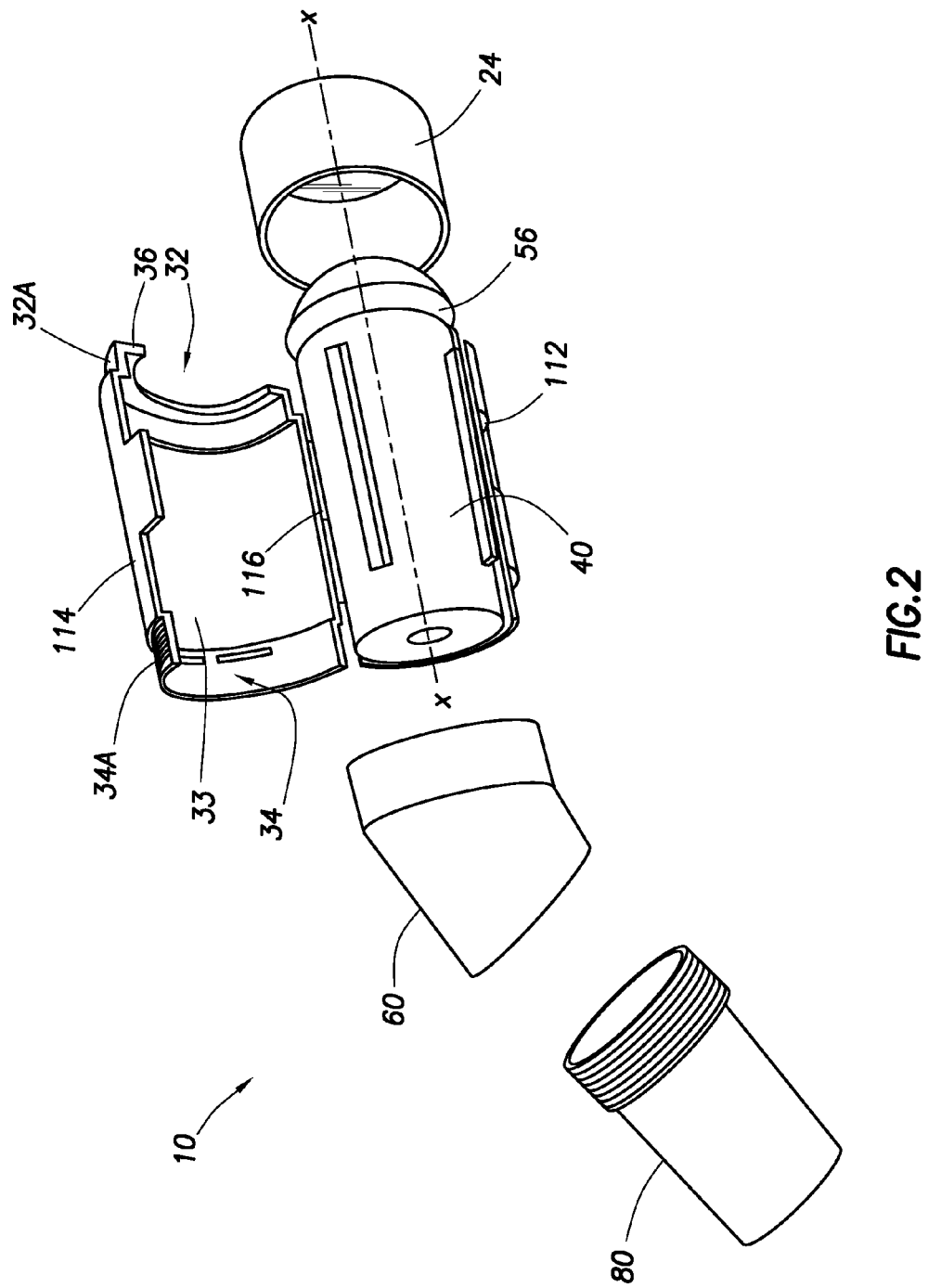
FIG. 2 is a disassembled exploded perspective view of another embodiment of the system of the disclosure.

Device 20 may include shell 22 and sleeve 40. As illustrated in FIGS. 1 and 2, shell 22 may comprise a single-piece (FIG. 1) or multiple-piece (FIG. 2) embodiment. The multiple-piece embodiment may be referred to as a "clam-shell" structure. The embodiment of FIG. 2 is illustrated in the open configuration to display the interior features of the shell 22. The multiple-piece embodiment in FIG. 2, when closed, may appear substantially the same as the single-piece embodiment of FIG. 1 with respect to the exterior features thereof. Conversely, the interior features of the single-piece embodiment of FIG. 1 may be substantially the same as the multiple-piece embodiment of FIG. 2. Shell 22 may form a first opening 32 and a second opening 34 with a central passage 33 and corresponding first and second ends 32A and 34A. Referring again to FIG. 1, in the embodiment illustrated, an outside surface of the shell 38 also includes features 39 to assist with gripping the shell.

In at least some embodiments, shell 22 retains the sleeve. Further, the sleeve may be removably disposed within the shell or an integral part thereof. Yet further (FIG. 2), shell 22 may be bifurcated into a first 112 and second 114 portion and hingedly 116 connected. The multiple-piece shell embodiment of system 10 will be further described on conjunction with FIG. 7 below.

Still referring to FIGS. 1 and 2, in at least some embodiments at least one of shell 22 and sleeve 40 is configured to retain the other such that the sleeve and the shell are constrained from substantially sliding longitudinally in either direction (i.e., reciprocatively) with respect to the other as along an axis x-x (FIG. 2). For example, shell 22 may comprise one or more features which mateably connect, couple, or otherwise act to keep sleeve 40 from substantially longitudinally moving therein. In the illustrated embodiment in FIG. 2, a ring 36 is provided to be received within an annular groove 56 forming a recession in sleeve 40, however other features, protrusions or similar devices may be used. When mateably received therein, the sleeve and the shell are substantially constrained from reciprocatively sliding longitudinally with respect to one another during use.

Shell 22 may be designed and constructed to mate with removable covers or caps 24 and 86. Cap 24 may be configured to threadably mate with end 32 of shell 22. Other connections may be equivalently used, such as telescoping connections, as well as partial-turn positive locking systems. Cap 86 (FIG. 1) may be designed and constructed to threadably mate with end 34 of shell 22, as, for example, when system 10 is stored while not in use. Yet further, the shell may be configured in appearance in any manner, from and including sexually suggestive, to inconspicuous.

In the illustrative examples of FIG. 1 and FIG. 2, the shell 22, adapter 60, and receptacle 80 comprise mateable threads such that the adapter removably connects the shell 22 to the receptacle 80. Other connecting fittings or fixtures may be used (e.g., a bayonet fitting), and such fixtures would fall within the spirit and scope of the present inventive principles.

FIG. 3 shows a cross-sectional elevation view of the system 10. In particular, FIG. 3 shows an elongate, flexible, polymeric, and compressible sleeve 40 (e.g., an insert) comprising first end 42 and second end 44. First end 42 defines a first orifice 48, and second end 44 defines a second orifice 50. Sleeve 40 defines an elongate channel 46 between the first orifice 48 and second orifice 50. In the example system shown, the elongate channel 46 is defined along a central axis of the sleeve 40, with central axis being perpendicular to planes defined by the outer-most features of the first and second orifices 48 and 50. However, the elongate channel need not reside along the central axis of the sleeve 40.

In one embodiment, the passage 46 is sized so to accommodate the human penis. The first orifice 48 receives the penis, and the passage 46 sized (e.g., diameter) being smaller than the girth of the penis so as to contact, circumferentially, and stimulate the penis. Further, the sleeve or insert 40 may be formed from any suitable material which simulates human flesh (i.e., of the type forming sexually receptive orifices). For example, the sleeve 40 may be made of thermoplastic elastomer (TPE) gel, silicon, polyvinyl chloride (PVC), or elastomeric rubber, to name a few. Suitable elastomeric gels have been described in the above-referenced U.S. Pat. No. 5,782,818. Sleeve 40 may be removably placed inside chamber of the shell 22 upon removal of the cap 24. In another embodiment, the passage 46 is sized so to accommodate a non-human penis (e.g., a horse, dog).

As illustrated by FIG. 3, a receptacle 80 for holding, capturing, receiving and/or storing collected seminal or other fluid is coupled to adapter 60 (such as by a threaded connection), and the adapter 60 is coupled to the sleeve 40. In the example system, the adapter couples to the sleeve 40 by way of shell 22, but in other cases a shell 22 need not be used and thus the adapter 60 may couple directly to the sleeve 40. The receptacle 80 defines an interior volume 83, and when coupled as shown in FIG. 3, the passage 46 is fluidly coupled to the interior volume 83.

Adapter 60 in the illustrated embodiment forms an angle as measured from a first end 62 to a second end 64. The adapter 60 may be angled (shown as a in FIG. 3), from 100 degrees to 170 degrees in one embodiment, from 110 degrees to 160 degrees in another embodiment, and from 120 degrees to 150 degrees in a third embodiment. Thus, when receptacle 80 is coupled to device 20, receptacle 80 is disposed at an angle to and extends below, or away from, a central axis of passage 46. The angle α may be measured at any suitable location, such as in reference to a side of the adapter 60 as shown. In other cases, the angle α may be measured as the angle between a central axis formed by a first end of the adapter 60 (e.g., the end that couples to the shell 22) to a central axis formed by a second end (e.g., the end that couples to the receptacle 80).

FIG. 4 shows a side elevation view of a receptacle 81 in accordance with another embodiment. In particular, receptacle 81 defines a first open end 82 and an interior volume 83. In the example embodiment of FIG. 4, the adapter 60 may be omitted, and the receptacle 81 coupled to directly or indirectly to the sleeve 40. Thus, in the embodiment of FIG. 4, the receptacle 81 itself defines a transition region 85 such that the receptacle is angled from the first end 82 to a second end 84. The transition region 85 may be angled (shown as A in FIG. 4) from 100 degrees to 170 degrees in one embodiment, from 110 degrees to 160 degrees in another embodiment, and from 120 degrees to 150 degrees in a third embodiment. In at least some embodiments, the angle, A, may be defined between a first central axis, 1-1" perpendicular to a plane defined by the outermost feature of end 82 and a second central axis 2-2" perpendicular to a plane defined by the outermost feature of end 84.

In example systems, the receptacle is further configured to removably accommodate a cap 87. Cap 87 may include threads or other fittings suitable to mate with the threads or other fittings provided with receptacle 81 to mateably couple to shell 22. In at least some embodiments of receptacle 81, the threads (e.g., threads 89) or other fittings are disposed on an exterior surface of the adapter. Thus, cap 87, when in place on receptacle 81 after use isolates interior volume 83 thereof and secures the contents against loss or contamination. Although cap 87 has been described in conjunction with receptacle 81, cap 87 may equally be configured to removably mate with an embodiment in accordance with receptacle 80 wherein cap 87 includes threads or other fittings suitable to mate with the threads or other fittings provided with receptacle 80 to mateably couple to adapter 60.

Figure 5B:
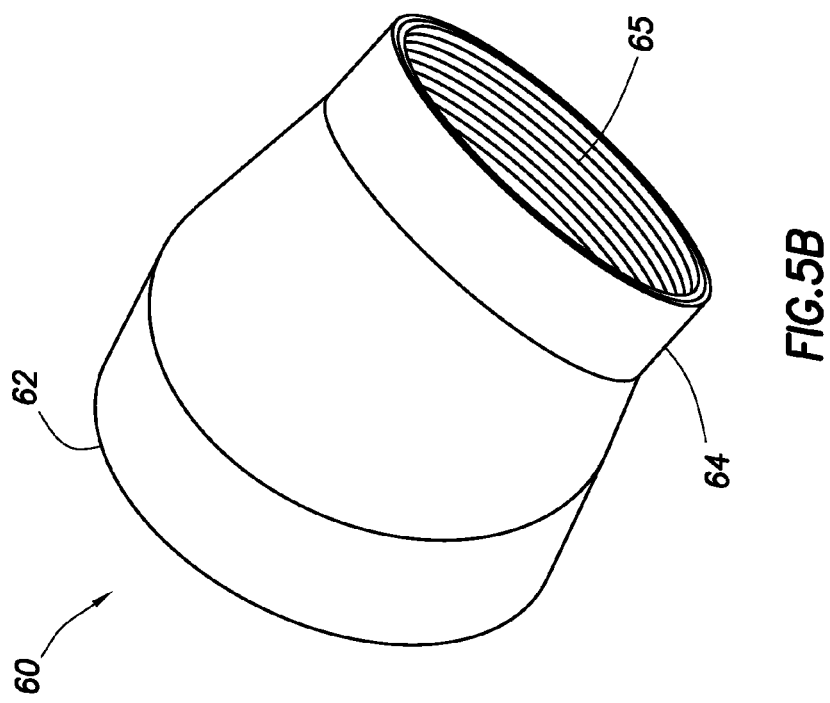
FIGS. 5A and 5B illustrate multiple views of an adapter according to one embodiment of the disclosure.
Figure 5A:
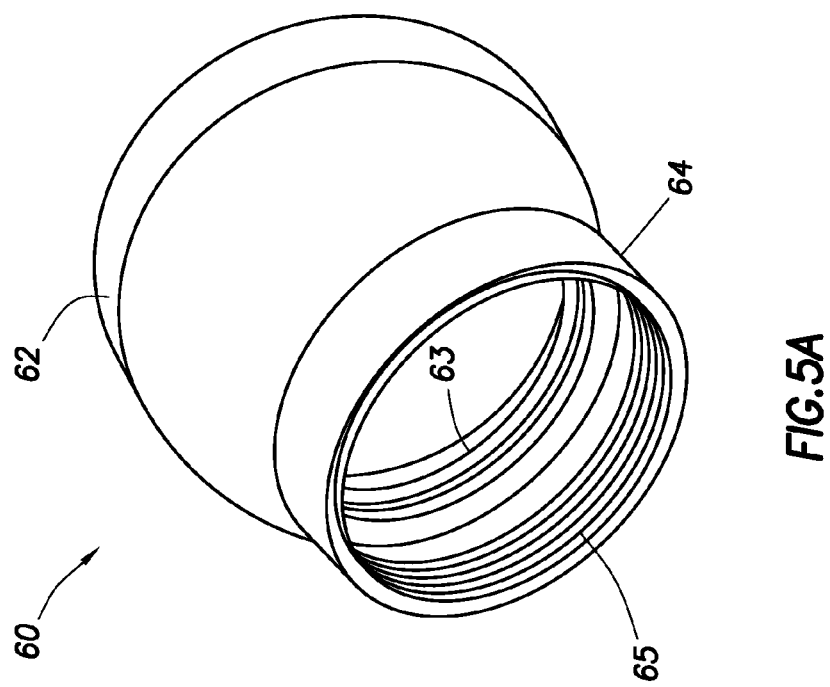

FIGS. 5A and 5B depict various perspective views of adapter 60 in accordance with example systems. In particular, FIGS. 5A and 5B show that in some embodiments, the adapter 60 defines a first end 62 which is configured to couple to the system 20, such as by threads 63. The adapter 60 further comprises a second end 64 which is configured to couple to a receptacle 80 (not shown in FIGS. 5A and 5B) such as by threads 65. In some cases, the diameter of the aperture defined in the first end 62 is larger than the diameter of the aperture defined in the second end 64, but in the other cases the relative size may be the same, or the aperture defined in the second end 64 may be larger. Again, threaded connections are examples, and other connection types may be used.

FIGS. 6A-6E shows various perspective views of adapter 60 in accordance with another example embodiment. In the embodiment depicted in FIG. 6A-6E, adapter 60 may structurally be similar to the adapter of FIGS. 5A and 5B, but may further comprise a vent in the form of an aperture 66 through a sidewall of the adapter 60. The aperture 66 enables pressure equalization between an interior volume of the system 10 and atmospheric pressure. In order to prevent loss of bodily fluids, in most cases the aperture 66 is disposed on an upper surface 67 of the adapter; however, alternate configurations and locations for aperture 66 are also possible as long as the aperture provides for and enables for the release of entrained air. Further, a user can regulate the rate at which the pressure equalizes by obstructing or partially obstructing the aperture using, for example, a finger or thumb. In this way, a partial vacuum may be produced within system 10, and the suction created thereby can aid in the expulsion of seminal fluid. Vacuum control may aid in the collection of a specimen from a patient whose ejaculation is weak, for example. Alternatively, in another embodiment, a plug (not shown) having a hole or aperture therein may be provided, wherein the plug may be inserted in vent 66, and wherein the aperture is sized such that the flow of air between the interior volume of system 10 and the exterior is controlled to maintain the partial vacuum in the interior volume. In this way, the plug plays the role of the user's finger or thumb. Further, the plug may be provided with a snap fitting or fixture or similar structure to retain the plug in the vent during use of system 10.

In FIG. 6A the angled aspect of adapter 60 is shown in further detail. In at least some embodiments, the angle, α as described above in conjunction with FIG. 3, may be defined between a first central axis, 1-1" perpendicular to a plane defined by the outermost feature of end 62 and a second central axis 2-2' perpendicular to a plane defined by the outermost feature of end 64.

Figure 7A:
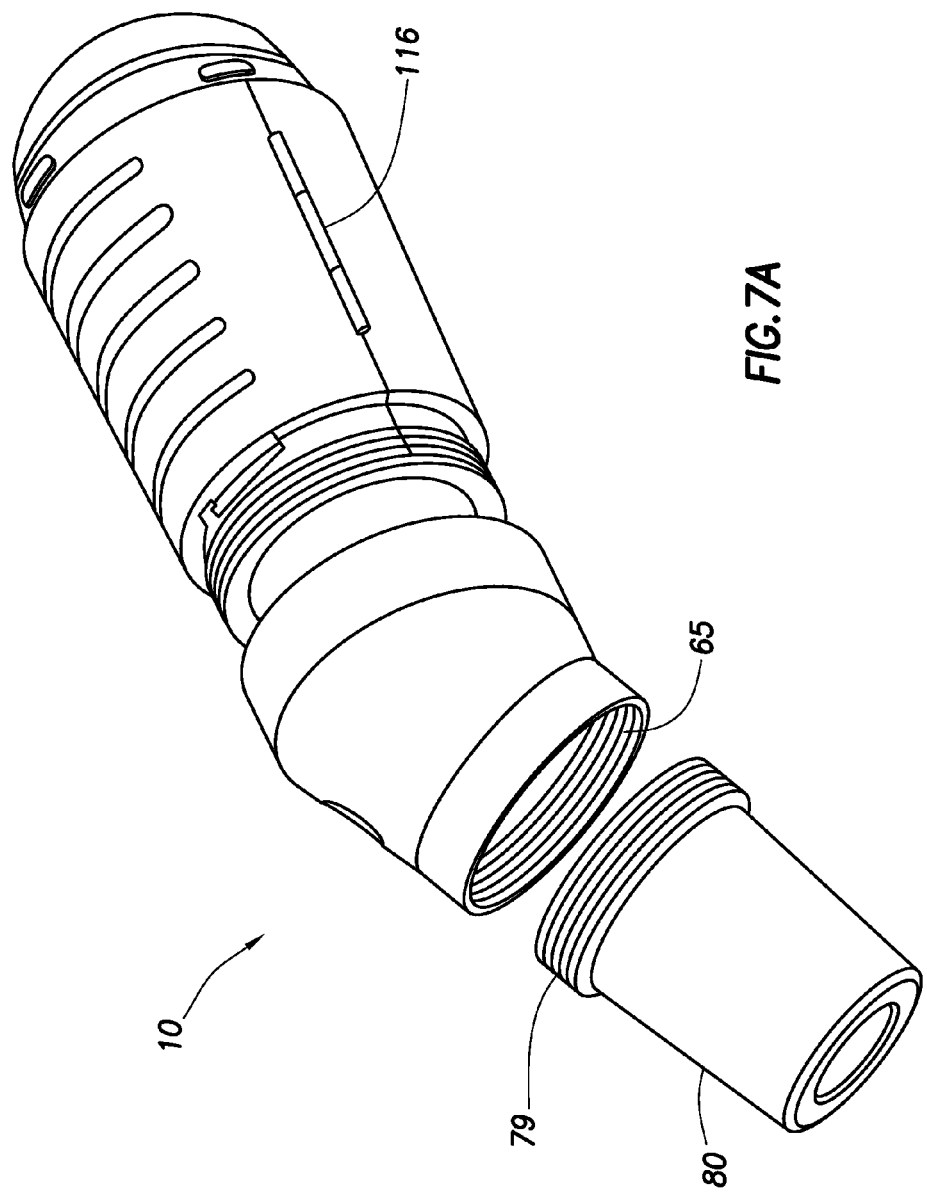
FIG. 7A illustrates a disassembled exploded perspective view of the system of FIG. 2.
Figure 7B:
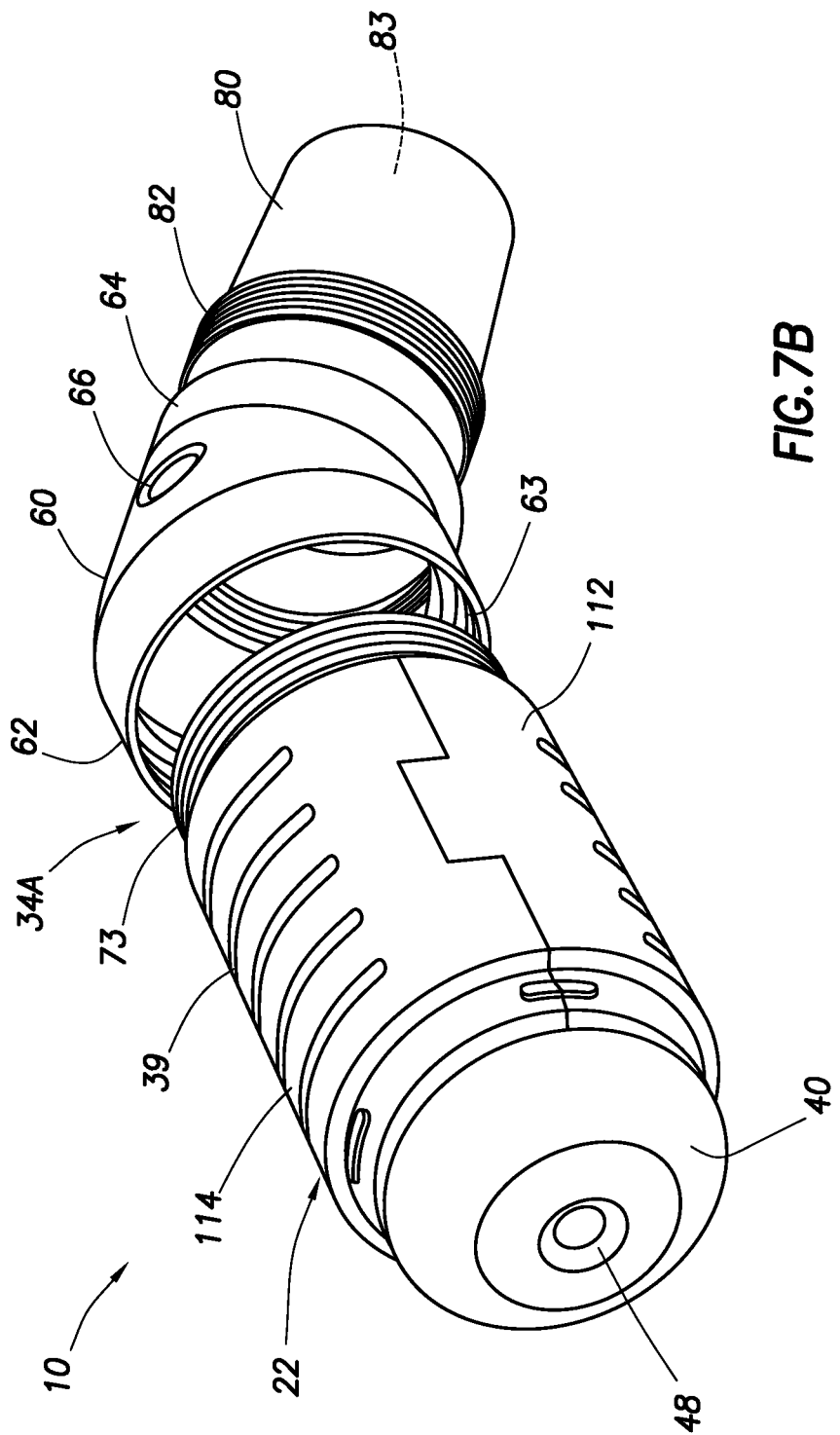
FIG. 7B illustrates a disassembled exploded perspective view of the system of FIG. 2.

FIGS. 7A and 7B show two exploded perspective views of the system 10 in accordance with example clam-shell embodiments. In particular, sleeve 40 is disposed within shell 22, which shell 22 is comprised of two portions, portion 112 and portion 114 connected via hinge 116. Adapter 60 removably couples receptacle 80 to shell 22 via threads 73, 63, 65 and 79. The embodiment of adapter 60 shown in FIG. 7 includes vent 66.

FIGS. 8A and 8B illustrate a flowchart of a method in accordance with an embodiment of the disclosure. Referring first to FIG. 8A, the method, collecting seminal fluid from a mammalian male, starts at block 800. In block 802, the mammalian male is stimulated to ejaculation. The seminal fluid is received within a passage of an elastomeric sleeve, block 804. The elastomeric sleeve is oriented such that the seminal fluid is gravity fed to a receptacle, block 806. In block 808, the receptacle is removed from coupling with the elastomeric sleeve, and, in block 810 a cap is placed on the receptacle. The method ends at block 812.

Referring now to FIG. 8B, illustrated therein is the method of block 802 in further detail. The mammalian male is stimulated in block 801. During at least a portion of the stimulation, the interior volume of the receptacle is vented to atmospheric pressure, block 803, such as through aperture 66. However, during ejaculation, pressure within the interior volume is reduced, block 805. Reduction of pressure (e.g., creating a pressure less than atmospheric pressure) may involve blocking the aperture 66 at the point the penis is inserted into the sleeve, and then partially retracting the penis from the sleeve while holding the aperture 66 in a blocked configuration. The increased volume defined between the penis and receptacle 80, without the introduction of airflow in the aperture 66, results in creation of pressure in the interior volume which is less than atmospheric. The lowered pressure may act to force greater seminal fluid flow, and greater sperm flow, (compared a vented system) than the situation where the seminal fluid is ejaculated to an atmospheric pressure receptacle 80.

In use, if not assembled, the system 10 is assembled by inserting the sleeve 40 into the shell 22. Further, in embodiments having a clam-shell design, by assembling or closing the shell to form the openings 32 and 34 at respective ends 32A and 34A. The first end 62 of the adapter 60 can then be connected to the second end 34A of the shell 22; and the second end 64 of the adapter 60 can be coupled to the first end 82 of the receptacle 80. This configuration then enables the fluid communication from the first orifice 48 to the interior 83 of receptacle 80. The penis is then inserted into the sleeve 40 and mechanically manipulated until ejaculation, wherein the specimen flows into and is collected in receptacle 80. Receptacle 80 can then be detached from the adapter 60 and covered with the cap 87 for analysis, use, sale, and/or distribution. The system can then be cleaned and either a new or reused receptacle 80 can be used for repeated usage of system 10.

The above discussion is meant to be illustrative of the principles and various embodiments of the present invention. Numerous variations and modifications will become apparent to those skilled in the art once the above disclosure is fully appreciated. For example, end caps are not essential to the use of the system. It is intended that the following claims be interpreted to embrace all such variations and modifications.

What is claimed is:

1. A device comprising:
   a sleeve of elastomeric material, the sleeve defines:
      first and second ends, each end comprising respectively a first and a second orifice; and
      a passage extending between the first and second orifices;
   a receptacle comprising:
      a side wall and a bottom that define an interior volume;
      the receptacle mechanically coupled to the sleeve such that the interior volume is fluidly coupled to the passage of the sleeve; and
   a shell configured to enclose the sleeve, the shell sleeve and receptacle configured to sustain a partial vacuum generated upon retraction of a mammalian penis inserted in the sleeve;
   wherein the device further comprises a vent between the passage and the receptacle, the vent, when unblocked, fluidly couples the interior volume to atmospheric pressure.

2. The device of claim 1 wherein the device further comprises an adapter configured to fluidly couple the passage of the sleeve to the receptacle, and wherein the vent comprises an orifice in the adapter.

3. A system comprising:
   an elongate flexible sleeve comprising first and second opposite ends, each end comprising first and second orifices, respectively, the sleeve comprising an elongate passage extending between and connecting the first and second orifices;
   a shell configured to removably retain the sleeve, the shell comprising first and second openings corresponding to the respective first and second orifices;
   a cap configured to couple to and cover the first opening of the shell; and
   a receptacle that defines an interior volume, the receptacle configured to be removably coupled to the shell so as to be in fluid communication with the second orifice when so coupled and comprising a connection fixture disposed on an exterior surface thereof and configured to removably accommodate a device for sealing the interior volume; and wherein
   the shell, flexible sleeve, and receptacle are configured to sustain a partial vacuum generated upon retraction of a mammalian penis inserted in the sleeve;
   wherein the adapter further comprises a vent for the release of entrained air within the device.

4. A method comprising:
   collecting seminal fluid from a mammalian male by:
      stimulating, to ejaculation, the mammalian male by reciprocatory motion of an elastomeric sleeve relative to a penis of the mammalian male inserted into the sleeve;

receiving the seminal fluid within a passage of the elastomeric sleeve;

orienting the elastomeric sleeve such that the seminal fluid is gravity fed to a receptacle mechanically coupled to the elastomeric sleeve;

venting an interior volume of the receptacle to atmospheric pressure during at least a portion of the stimulating; and then reducing pressure within the interior volume during ejaculation by blocking a vent port.

5. The method of claim 4 wherein reducing pressure further comprising simultaneously blocking the vent port while decreasing the insertion distance of the penis into the elastomeric sleeve.

* * * * *